US006567525B1

(12) United States Patent
Sapiejewski

(10) Patent No.: US 6,567,525 B1
(45) Date of Patent: May 20, 2003

(54) SUPRA AURAL ACTIVE NOISE REDUCTION HEADPHONES

(75) Inventor: Roman Sapiejewski, Boston, MA (US)

(73) Assignee: Bose Corporation, Framingham, MA (US)

( * ) Notice: Subject to any disclaimer, the term of this patent is extended or adjusted under 35 U.S.C. 154(b) by 0 days.

(21) Appl. No.: 08/261,802

(22) Filed: Jun. 17, 1994

(51) Int. Cl.[7] ......................... A61F 11/06; G10K 11/16; H03B 29/00

(52) U.S. Cl. ...................... 381/71.6; 381/309; 381/371; 381/372; 381/373; 381/375

(58) Field of Search ............................ 381/71, 25, 183, 381/187, 72, 74, 71.6, 71.7, 309, 335, 370, 371, 372, 373, 374, 375, 384; 379/430; 181/129

(56) References Cited

U.S. PATENT DOCUMENTS 4,041,256 A * 8/1977 Ohta et al. .................. 381/187
4,088,849 A * 5/1978 Usami et al. ................. 381/25
4,160,135 A 7/1979 Gorike
4,572,324 A * 2/1986 Fidi et al. ................... 381/153
4,644,581 A * 2/1987 Sapiejewski ................ 381/183
4,965,836 A * 10/1990 Andre et al. .................. 381/25
5,208,868 A 5/1993 Sapiejweski

FOREIGN PATENT DOCUMENTS

| | | | | |
|---|---|---|---|---|
| DE | 28 15 051 A1 | | 10/1978 | |
| EP | 0 208 389 | | 1/1987 | |
| GB | 2188210 | * | 9/1987 | ................. 381/183 |
| JP | 0041219 | * | 4/1978 | ................. 381/183 |
| WO | WO93/26084 | | 12/1993 | |

OTHER PUBLICATIONS

Yamahayh–1/2/3 Apr. 1983.*
EPO Search Report, Mar. 25, 1996, Europeant Patent Office.

* cited by examiner

*Primary Examiner*—Ping Lee
(74) *Attorney, Agent, or Firm*—Fish & Richardson P.C.

(57) ABSTRACT

A supra aural headphone including an earphone that includes a shell body, a cushion mounted on the shell to thereby define an internal cavity behind the cushion, and an acoustical driver mounted within the internal cavity to reproduce sound for the user when driven by an audio signal. The cushion has a passageway extending therethrough which acoustically connects the internal cavity with a user's ear cavity when the cushion is resting on the user's ear while being worn by the user. The internal cavity has a total volume that is larger than about 10 cubic centimeters, and the driver is mounted in such a way as to avoid obstructing the passageway.

31 Claims, 3 Drawing Sheets

SUPRA AURAL ACTIVE NOISE REDUCTION HEADPHONES

BACKGROUND OF THE INVENTION

The invention generally relates to headphones that are designed to provide noise attenuation.

There are at least three headphone design types, which are generally categorized in terms of how they are worn by the user. The three design types are referred to as around-the-ear in-the-ear, and on-the-ear designs. Around-the-ear headphones have large earphones that resemble earmuffs. Like earmuffs, the around-the-ear earphone covers and surrounds the ear. They typically provide very good noise attenuation but they are not particularly comfortable, especially for people using eyeglasses. Since the earphone surrounds the user's ear, it cuts off air circulation behind the ear and thus can be uncomfortably warm in hot weather.

Under some circumstances, the around-the-ear of headphones actually provide too much noise attenuation. There are environments or applications in which it is in fact desirable to hear some external sound, for example, in certain industrial applications and in airplanes. In large industrial plants where a lot of machine noise is present, it may be useful to use radios as a way of communicating with coworkers located elsewhere in the plant. Because of the high noise levels, earphones must be worn to hear the radio communications. To be effective, the earphones must also block out some of the external noise. But if they block out too much of the external noise, the user will not be able to hear the conversations of nearby coworkers or the helpful sound queues of operating machinery. In airplanes, the airline pilot needs headphones that effectively block out the external engine noises. But the pilot also needs to hear the conversation of people who are nearby, such as their copilot or other airline support staff. In those applications, the around-the-ear headphones sometimes work to well.

The in-the-ear headphone which typically provides less attenuation than the around-the-ear type has an ear piece that fits into the ear cavity, i.e., concha. Unlike the around-the-ear design, the in-the-ear headphone is typically very light and compact. For some people, they are also very comfortable. A significant number of other people, however, are either unwilling to insert an earpiece into their ear because they have sensitive ears or they (e.g. children) have an ear size that is not large enough to accommodate the ear piece. For that group of people, the in-the-ear design is not appropriate.

The third design (i.e., the on-the-ear design) is less intrusive than the other two. According to this design, also referred to as the supra aural design), each earphone has a cushion that simply rests on the ears when the headphone is being worn by the user. Typically, the cushion is made of an open cell foam material that easily transmits sound. This design tends to be lightweight, compact, and very comfortable. One disadvantage, however, is that conventional on-the-ear designs do not very effectively attenuate external noise. Thus, they are not well suited for use in noisy environments.

SUMMARY OF THE INVENTION

In general, in one aspect, the invention is a supra aural headphone including an earphone, which includes a shell body, a cushion mounted on the shell to thereby define an internal cavity behind the cushion, and an acoustical driver mounted within the internal cavity which during use reproduces sound when driven by an audio signal. The cushion has a passageway extending therethrough so as to acoustically connect the internal cavity with a user's ear cavity when the cushion is resting on the user's ear while being worn by the user. The internal cavity has a total volume that is larger than about 10 cubic centimeters so as to passively attenuate any external sound which leaks through the earphone to the user's ear cavity, and the acoustical driver is mounted within the internal cavity in such a way as to avoid obstructing the passageway which acoustically connects the internal cavity with the user's ear cavity.

In preferred embodiments, the total volume of the internal cavity is substantially larger than about 10 cc, e.g. an order of magnitude larger than 4 cc. The cushion has a back side and a front side and the passageway forms an opening in the front side having a diameter that is less than about 15 mm in size (e.g. within a range of about 10 to 15 mm). The passageway increases in diameter as it passes through the cushion from the front side to the back side. The internal cavity is partially filled with an acoustic damping material. The driver is offset from the central axis of the passageway (e.g. it lies completely off of the central axis). The driver lies in a plane that is inclined with respect to the central axis.

Preferred embodiments also include an acoustical microphone mounted within the internal cavity, which during use provides a feedback signal for an active noise reduction circuit. The microphone is mounted in front of the driver and offset from the center of the driver. More specifically, the microphone lies in a first plane and the driver lies in a second plane and the first plane is substantially perpendicular to the second plane. Also, the passageway forms an opening in the back side of the cushion and the second plane (i.e., the driver plane) is inclined with respect to the opening in the back side of the cushion so that the microphone extends into the passageway.

Also in preferred embodiments, there is a driver support structure which defines a smaller cavity behind the driver when the driver is assembled onto the support structure. The smaller cavity is within and separate from the first-mentioned cavity and it is acoustically isolated from the first-mentioned cavity except for a pressure equalization hole interconnecting them. In addition, a wall of the smaller cavity is formed by a portion of the shell body which also includes a hole connecting the smaller cavity to outside of the shell body. The hole connecting the smaller cavity to the outside is covered by an acoustically resistive screen. The cushion is made of a molded, self skinned, damped, compliant material.

In general, in another aspect, the invention is a supra aural headphone including an earphone that includes a shell body having an inside and an outside; and a cushion mounted on the shell. The cushion and the inside of the shell defines an internal cavity behind the cushion. The cushion includes a passageway extending therethrough so as to acoustically connect the internal cavity with a user's ear cavity when the cushion is resting on the user's ear while being worn by the user. The internal cavity has a total volume that is larger than about 10 cubic centimeters.

In general, in yet another aspect, the invention is a supra aural headphone including an earphone, that includes a shell body, a cushion mounted on the shell to thereby define an internal cavity behind the cushion, an acoustical driver mounted within the internal cavity which during use reproduces sound when driven by an audio signal, and an acoustical microphone mounted within the internal cavity, which during use provides a feedback signal for an active noise reduction circuit. The cushion has a passageway extending therethrough so as to acoustically connect the internal cavity with a user's ear cavity when the cushion is resting on the user's ear while being worn by the user. The internal cavity has a total volume that is larger than about 4 cubic centimeters. The acoustical driver is mounted within the internal cavity in such a way as to avoid obstructing the passageway which acoustically connects the internal cavity with the user's ear cavity.

The supra aural (on-the-ear) configuration provides comfortable, lightweight and easy to use headphones which attenuate ambient noise and reproduce high quality signals. Noise attenuation is achieved by both passive and active means. Passive attenuation is achieved by using very soft, self skin, highly damped foam cushions and by using a large volume cavity behind the cushion. Active attenuation is achieved by acoustic feedback methods.

Headphones designed in accordance with the invention provide flat attenuation of about 15–20 db over a broad frequency range. This is sufficient to significantly attenuate external noise but not so much as to block all sound such as the conversation of a nearby person. In addition, such headphones are also considerably smaller and lighter than alternative designs which provide comparable attenuation.

Since they rest on the ear without compressing the ear against the head, the back of the ear remains exposed to circulating air thereby resulting in better heat dissipation. Thus, the headphone of the present invention offers attenuation characteristics comparable to the around-the-ear designs but without the discomfort in hot weather.

Other advantages and features will become apparent from the following description of the preferred embodiment and from the claims.

DESCRIPTION OF THE PREFERRED EMBODIMENTS

Figure 1:
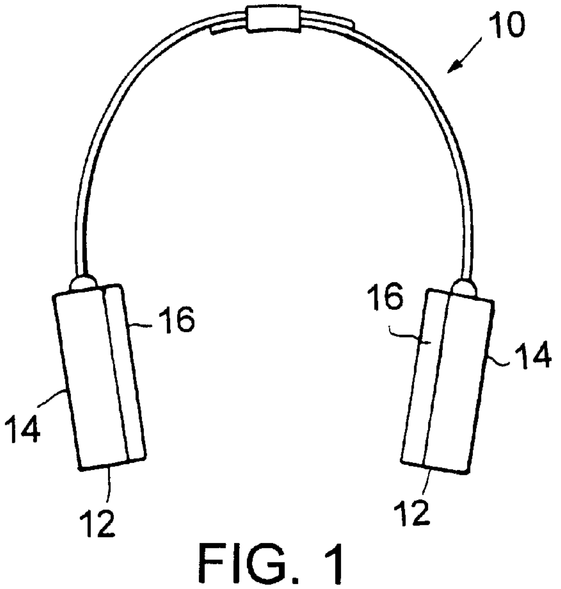
FIG. 1 shows a headphone with two supra aural earphones.
Figure 2:
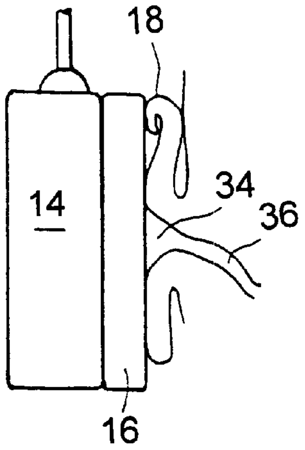
FIG. 2 is a side view of the supra aural earphone on a persons ear.

Referring to FIGS. 1 and 2, a supra aural headphone 10 which embodies the invention includes two earphones 12, one for each ear. Each earphone 12 includes a rigid shell 14 which houses a driver and a microphone (not shown in FIGS. 1 and 2) and it includes a soft cushion 16 which rests against the ear 18 when the headphones are worn by a user. The cushion is made of a soft, molded, self skinned, heavily damped highly compliant material. By self skinned, we mean that the surface of the cushion is smooth so that it forms a good seal with the ear when it is resting against the ear. By heavily damped, we mean a material that has low sound transmission capability. Typically, a heavily damped material exhibits a slow recovery rate (e.g. on the order of seconds) to its original shape after being compressed. By highly compliant, we mean that the material is soft and conforms readily to the human ear without having to apply much pressure. A suitable material which exhibits all of these properties is a urethane foam, such as is described in U.S. Pat. No. 4,158,087, or any other comparable material.

Figure 3:
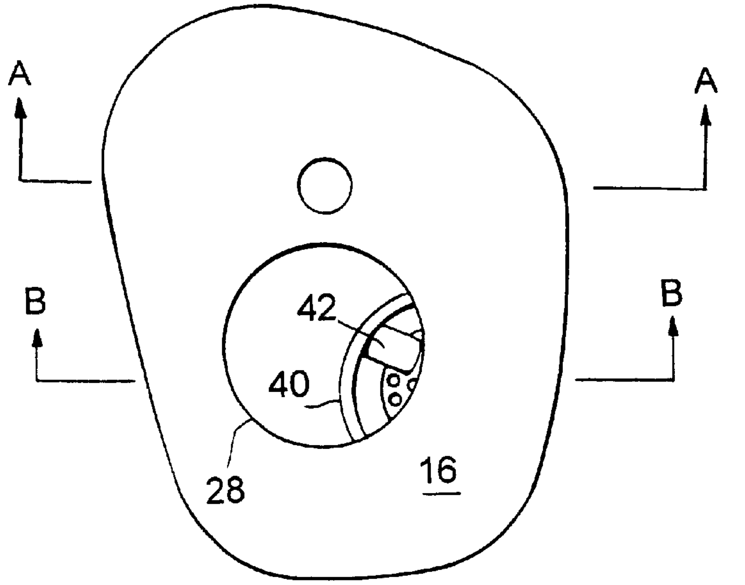
FIG. 3 shows the cushion side of the earphone.
Figure 4:
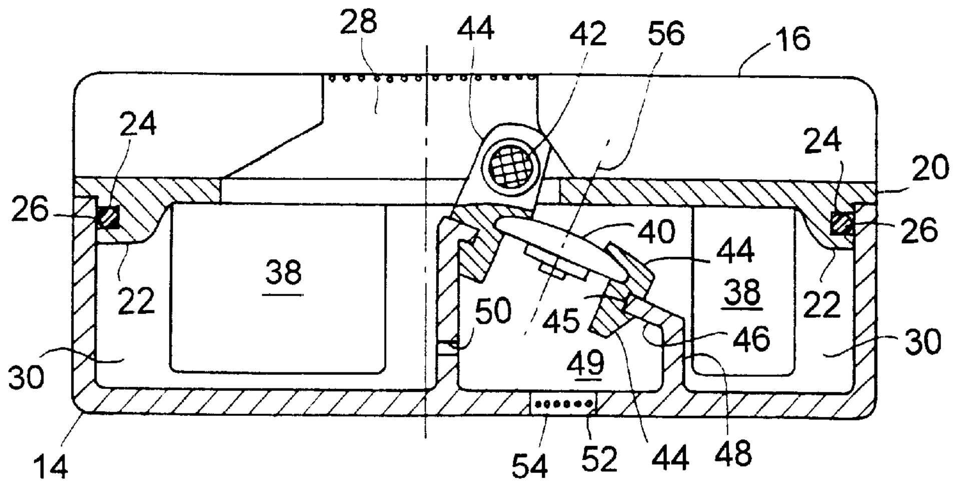
FIG. 4 shows a cross-sectional view of the earphone through section A—A of FIG. 3.

Referring to FIGS. 3 and 4, cushion 16 is attached to a rigid plate 20 that is, in turn, mounted on shell 14. Around the outer perimeter of plate 20, on a side opposite to the side on which the cushion is attached, there is raised shoulder 22 that has a groove 24 formed in it. In the groove there is an o'ring 26. When plate 20 is assembled onto shell 14, shoulder 22 with the o'ring 24 slides into the shell and forms a seal around its outer perimeter.

Cushion 16 has a hole 28 passing through it which connects a large cavity 30 within the shell behind the cushion to the outside. On the side of the cushion which rests against the listener's ear, the hole forms a relatively large diameter circular opening. In fact, the larger the opening, the more effective the acoustic coupling between the ear cavity and cavity 30 within shell 16. If the opening is made too large, however, the cushion will not form a seal with the ear that completely surrounds the ear cavity and thus noise will not be effectively blocked out. Thus, it is desirable that the opening be as large as possible but not so large as to interfere with the cushion's ability to form a seal against the listener's ear stated in other words, the cross sectional area of the hole or passageway 28 is less than that of cushion 16 by an amount so that the portion of cushion 16 surrounding the ear cavity forms a seal against the listener's or user's ear when resting on the user's ear. To produce significant passive attenuation above 1,000 Hz an opening of about 10–15 mm is used. To increase the effective acoustical diameter of the hole beyond this, the passageway tapers outward as it passes through the cushion to form a larger diameter opening on the opposite side of the cushion.

The volume (i.e., acoustical volume) of cavity 30 within shell 16 is approximately an order of magnitude larger than the volume of the ear cavity, i.e., the combined volume of the concha and the ear canal. On an average adult, the volume of the ear cavity is about 4 cc (cubic centimeters), thus in the described embodiment the volume of the cavity in the shell is about 40 cc. It should be noted that the larger the volume of the cavity, the greater the attenuation of the sound that leaks past the cushion from the outside. Theoretically, a volume that is about ten times the combined volume of the ear cavity will produce an attenuation of about 20 dB. The invention, however, is not limited to using cavity sizes which are that large; noticeable passive attenuation will occur with a cavity that has a volume of about 10 cc. or greater.

To improve the transfer function properties of the cavity, it is filled with an absorbent material 38 made of foam or fiber, such as Thinsulate™ which is available from 3M (Minnesota, Mining and Manufacturing Corporation). Damping material 38 produces a more predictable, smoother transfer function for cavity 30 and it tends to reduce cavity resonances.

A driver 40 and a microphone 42 are mounted inside shell 16 and close to the hole that passes through the cushion. Both driver 40 and microphone 42 are held within separate, corresponding openings formed within a rubber or silicone grommet 44. Grommet 44 is, in turn, pressed into an opening 45 in a slanted or inclined top 46 of a cylindrically shaped structure 48. The cylindrically shaped structure 48 defines a smaller, internal driver cavity 49 located behind driver 40.

The flexible grommet facilitates easy assembly and it creates an excellent acoustical seal around the driver. When the grommet with the driver mounted in it is fitted into hole 45, the smaller cavity behind the driver is completely isolated from the larger cavity except for a small pressure equalization hole 50 in the side of the cylindrically shaped structure 48. Behind the driver, there is a circular opening 52 in the backside of the shell connecting the smaller cavity to the outside. The circular opening 52 is covered by an acoustically resistive mesh 54 providing an acoustic resistance of about $1\text{–}2\times10^{7}$ acoustic ohms.

The backside opening 52 is provided so that the low frequency performance of the driver is not diminished. The resistive mesh across the opening provides passive attenuation of higher frequency noise passing through the driver from the outside.

The pressure equalization hole, which also has an acoustic resistance of about $1\text{–}2\times10^{7}$ acoustic ohms, enables the pressure within the larger cavity 38 to equalize when the earphone is placed on the users ear. An alternative position for this hole is through the backside of the shell to the outside.

The grommet 44 holds the microphone so that the plane of the microphone is perpendicular to the plane of the driver and the microphone is offset from the central axis 56 of the driver. In addition, the microphone is oriented so that the central axis 56 of the driver lies in or close to the plane of the microphone. This orientation results in a minimum delay coupling between the microphone and the driver, and it produces optimum noise cancellation at a point lying between the front of the microphone and the front of the driver.

The slanted top 46 of the cylindrical structure 48 is inclined with respect to the opening in the support plate. When the grommet is fitted into place in the top, the microphone extends partially through the hole 28 and into the passageway passing from the cavity 30 behind the cushion to the ear cavity so as to position the microphone as close as possible to the listener's ear without obstructing the passageway.

In the described embodiment, the driver is a high compliance, high excursion driver (e.g. 15 mm or 20 mm diameter), such as Model TO16HO2 which is available from Foster of Japan. The microphone is a small diameter (e.g. 6 mm) electrical microphone such as the EM 109 electric microphone (or an equivalent device) which is available from Primo, Inc. of Japan.

Figure 5:
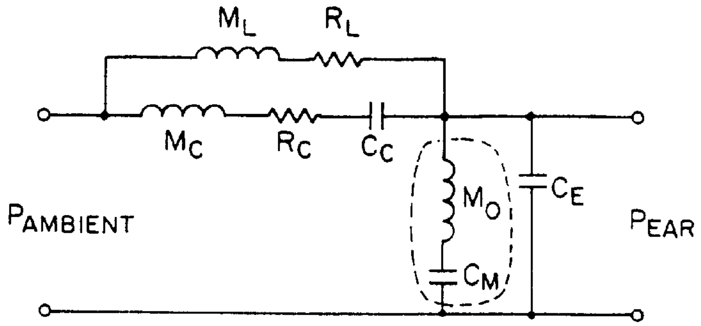
FIG. 5 is a circuit equivalent to the acoustical structure of the earphone.

In the headphones, passive attenuation is achieved by providing a mechanical structure which blocks ambient sound from entering the ear canal. A useful aid to visualizing how the invention solves the noise attenuation problem is an equivalent electrical circuit representation of the mechanical structure, as shown in FIG. 5.

In this circuit diagram, the identified signals and components have the following acoustical meaning:

$P_{AMBIENT}$=external sound pressure signal;

$P_{EAR}$=pressure signal reaching the ear;

$M_L$=mass of leak around cushion;

$R_L$=resistance of leak around cushion;

$M_C$=mass of cushion;

$R_C$=resistance of cushion;

$C_C$=compliance of cushion;

$C_E$=compliance of ear cavity;

$C_H$=compliance of headphone cavity volume; and $M_O$=mass of cushion opening.

The simplified circuit diagram represents the transmission of ambient sound into the ear as coming from two sources, namely, leakage between the cushion and the ear and transmission through the cushion itself. As can be seen from the circuit, for a given level of sound transmission through the leak and through the cushion, the sound pressure at the ear (i.e., $P_{EAR}$) is inversely proportional to the volume of the ear cavity under the cushion (i.e. the volume of the concha plus the volume of the ear canal). Thus, increasing this volume by adding a cavity behind the cushion reduces the sound pressure at the ear. In addition, the sound pressure at the ear is also inversely proportional to the damping of the cushion ($R_C$) and the leakage around the cushion ($R_L$). Thus, using a special self skinned, molded, cushion which is made of an extremely soft, highly damped material provides a good seal against the ear with little force and at the same time it also provides good attenuation of sound through the cushion itself.

Figure 6:
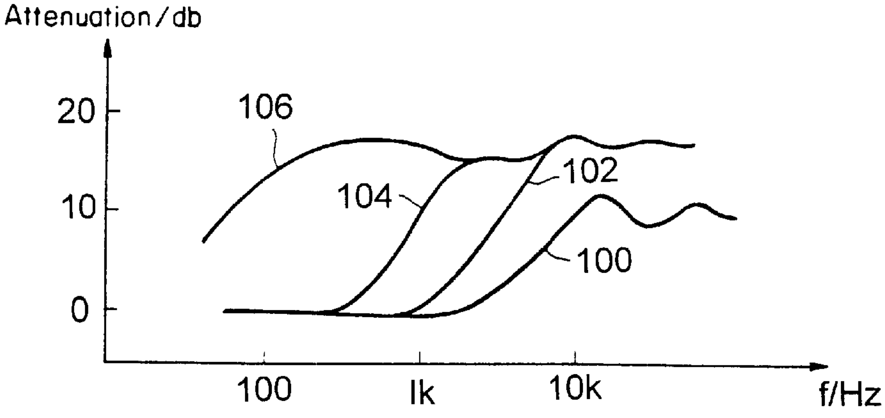
FIG. 6 illustrates the improvement in attenuation that is attributable to different aspects of the invention.

The performance improvements that result from the different features of the invention are illustrated in FIG. 6. Typically, the passive attenuation which is present in a headphone that has conventional on-the-ear earphones (i.e., a earphones without the special cushion and without the large cavity) is as shown in curve 100. There is very little attenuation at low frequencies and it becomes large only at high frequencies (e.g. frequencies above 5000 Hz). By using a special cushion, which has high sound damping properties and which has a self skinned surface that creates a good seal with the ear, the attenuation improves considerably beginning at frequencies above about 1000 Hz and extending to the higher frequencies (see curve 102). providing the larger volume behind the cushion extends the improvement in attenuation to frequencies below 1000 Hz as indicated in curve 104. Finally, the active noise reduction from the microphone-generated feedback extends the improved attenuation to frequencies well below 1000 Hz (see curve 106).

Figure 7:
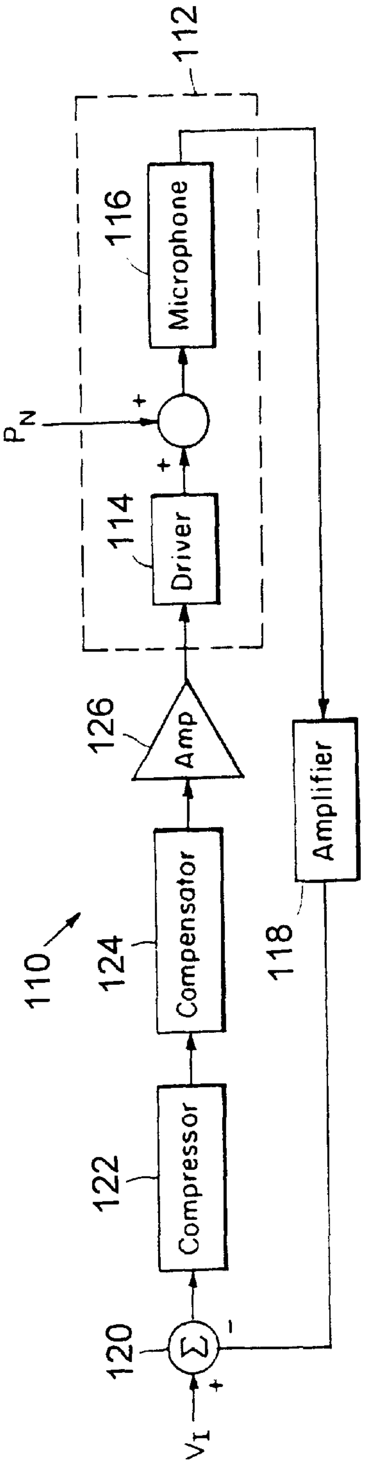
FIG. 7 is a block diagram of a system which includes the invention.

A circuit 110 which operates one of the earphones 112 in a headphone constructed in accordance with the invention is shown in FIG. 7. The circuit is duplicated for the other earphone of the headphone. Inside earphone 112 there is a driver 114 and a microphone 116. Driver 114 reproduces sound for a listener wearing the headphones and microphone 116 picks up low frequency ambient sound that is present in a cavity that exists between the earphone and the listener's ear. A preamplifier 118 amplifies the output signal from microphone 116 to produce a feedback signal that is fed back to a combiner circuit 120 at the input side of the circuit. Combiner circuit 120 adds the feedback signal to an input signal $V_I$, which represents the audio that is to be reproduced by the driver 114. The output of combiner circuit 118 passes first through a compressor circuit 122 which limits the amplitude of high level signals and then through a compensator circuit 124 which insures that the open-loop gain of the system meets the Nyquist stability criteria and thus does not oscillate.

The output of compensator circuit 124 passes to a power amplifier 126 and then to driver 114. Power amplifier 126 amplifies the signal to the level required for producing the desired sound level out of driver 114. The audio sound generated by driver 114 combines with ambient noise (identified as $P_N$ in FIG. 1) that leaks by the earphone cushion into the cavity formed between the earphone and the listener's ear. Thus, the signal that microphone 116 picks up represents the audio signal plus the ambient noise.

ALTERNATIVE EMBODIMENTS

Figure 8:
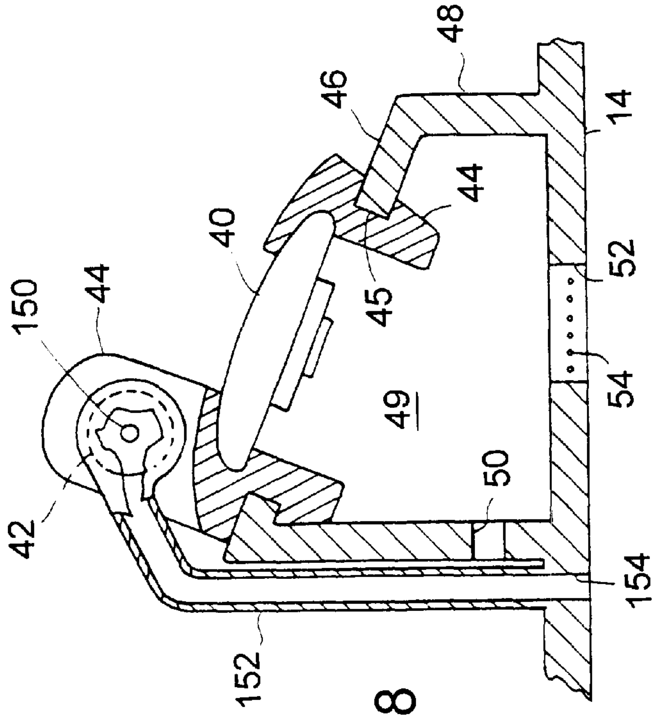
FIG. 8 shows an alternative design for the driver/microphone combination.

Referring to FIG. 8, in an alternative embodiment, microphone 42 is modified by drilling a hole 150 in its backside. (Note that this drawing shows the microphone mounted in such a way that its backside is visible in the drawing; whereas FIG. 3 showed it mounted so that its front was visible.) The hole 150 is acoustically coupled to the outside of the shell (or alternatively to cavity 49 behind the driver 40) through a conduit 152 and an equalization hole 154 in the wall of shell 14.

The advantage with this configuration is that the low frequency response of the microphone is no longer a factor from a system stability and control point of view and the clipping level of the system is increased at low frequencies. From an ambient noise point of view, the frequency response of the microphone will have first order roll-off (like a velocity microphone). The driver will have a flat frequency response at low frequencies. By proper selection of the size of the equalization hole 154, it is possible to increase the maximum level of the ambient noise that the system can accept before clipping. Typically the pressure equalization hole should be chosen to provide roll-off at about 30 Hz without significantly affecting cancellation above 100 Hz.

Other embodiments are within the following claims.

What is claimed is:

1. A supra aural headphone including an earphone, said earphone comprising:

a shell body having an inside and an outside;

a cushion having a front side and a back side mounted on the shell, said cushion and the inside of said shell defining an internal cavity behind the cushion, said cushion having a passageway extending therethrough so as to acoustically connect said internal cavity with a user's ear cavity when the cushion is resting on the user's ear contacting said front side while being worn by the user, the cross-sectional area of said passageway being less than that of said cushion by an amount so that the portion of said cushion surrounding the ear cavity forms a seal against the user's ear when resting on the user's ear, said internal cavity having a total volume, said total volume being larger than a volume of about 10 cubic centimeters so as to passively attenuate significantly external sound which leaks through the earphone to the user's ear cavity; and an acoustical driver constructed and arranged within said internal cavity to avoid obstructing said passageway, and wherein during use said driver is constructed and arranged to reproduce sound for the user when driven by an audio electrical signal.

2. The supra aural headphone of claim 1 wherein said total volume of the internal cavity is significantly larger than a volume of about 10 cc.

3. The supra aural headphone of claim 2 wherein the total volume of the internal cavity is a volume of at least about 40 cc.

4. The supra aural headphone of claim 1 wherein the passageway increases in cross-sectional area as it passes through the cushion from the front side to the back side.

5. The supra aural headphone of claim 1 further comprising an acoustic damping material within the internal cavity.

6. The supra aural headphone of claim 1 wherein passageway has a central axis and wherein the driver is offset from said central axis.

7. The supra aural headphone of claim 6 wherein the driver lies in a plane that is inclined with respect to the central axis.

8. The supra aural headphone of claim 1 wherein passageway has a central axis and wherein the driver lies completely off of said central axis.

9. The supra aural headphone of claim 1 further comprising a support structure for the driver, said support structure defining a driver cavity behind the driver when the driver is assembled onto the support structure, wherein said internal cavity is of larger volume than and surrounds said driver cavity.

10. The supra aural headphone of claim 9 wherein the driver cavity is acoustically isolated from the internal cavity except for a pressure equalization hole interconnecting them.

11. The supra aural headphone of claim 9 wherein a wall of the driver cavity is formed by a portion of the shell body and wherein said portion of the shell body includes a hole connecting the driver cavity to the outside of the shell body.

12. The supra aural headphone of claim 1 wherein the cushion is made of a molded, self skinned material.

13. The supra aural headphone of claim 1 wherein the cushion is made of a damped, compliant material.

14. A supra aural headphone including an earphone, said earphone comprising:

a shell body having an inside and an outside;

a cushion having a back side and a front side mounted on the shell body, said cushion and the inside of said shell defining an internal cavity behind the cushion, said cushion having a passageway extending therethrough so as to acoustically connect said internal front cavity with a user's ear cavity when the cushion is resting on the user's ear contacting said front side while being worn by the user, said internal cavity having a total volume, said total volume being larger than a volume of about 10 cubic centimeters so as to passively attenuate significantly external sound which leaks through the earphone to the user's ear cavity; and an acoustical driver constructed and arranged within said internal cavity to avoid obstructing said passageway, wherein during use said driver is constructed and arranged to reproduce sound for the user when driven by an audio electrical signal, and wherein the passageway forms an opening in the front side of said cushion having a diameter that is less than a diameter of about 15 mm in size.

15. The supra aural headphone of claim 14 wherein the passageway forms an opening in the front side of said cushions having a diameter that is within a range of about 10 to 15 mm in size.

16. A supra aural headphone including an earphone, said earphone comprising:

a shell body having an inside and an outside;

a cushion having a front side and a back side mounted on the shell, said cushion and the inside of said shell defining an internal cavity behind the cushion, said cushion having a passageway extending therethrough so as to acoustically connect said internal cavity with a user's ear cavity when the cushion is resting on the user's ear contacting said front side while being worn by the user, said internal cavity having a total volume, said total volume being larger than a volume of about 10 cubic centimeters so as to passively attenuate significantly external sound which leaks through the earphone to the user's ear cavity; and an acoustical driver constructed and arranged within said internal cavity to avoid obstructing said passageway, and wherein during use said driver is constructed and arranged to reproduce sound for the user when driven by an audio electrical signal, and further comprising an acoustical microphone mounted within said cavity, during use said microphone providing a feedback signal for an active noise reduction circuit.

17. The supra aural headphone of claim 16 wherein the microphone is mounted in front of the driver.

18. The supra aural headphone of claim 17 wherein the microphone is mounted in front of the driver and is offset from the center of the driver.

19. The supra aural headphone of claim 18 wherein the microphone lies in a first plane and the driver lies in a second plane and wherein the first plane is substantially perpendicular to the second plane.

20. The supra aural headphone of claim 19 wherein the cushion has a back side and a front side and wherein the passageway forms an opening in the back side and wherein the second plane is inclined with respect to the opening in the back side of the cushion.

21. The supra aural headphone of claim 20 wherein the second plane is inclined with respect to the opening in the back side of the cushion so that the microphone extends into the passageway.

22. A supra aural headphone including an earphone, said earphone comprising:

a shell body having an inside and an outside;

a cushion having a front side and a back side mounted on the shell, said cushion and the inside of said shell defining an internal cavity behind the cushion, said cushion having a passageway extending therethrough so as to acoustically connect said internal cavity with a user's ear cavity when the cushion is resting on the user's ear contacting said front side while being worn by the user, said internal cavity having a total volume, said total volume being larger than a volume of about 10 cubic centimeters so as to passively attenuate significantly external sound which leaks through the earphone to the user's ear cavity; and an acoustical driver constructed and arranged within said internal cavity to avoid obstructing said passageway, and wherein during use said driver is constructed and arranged to reproduce sound for the user when driven by an audio electrical signal, and further comprising a support structure for the driver, said support structure defining a driver cavity behind the driver when the driver is assembled onto the support structure, wherein said internal cavity is of larger volume than and surrounds said driver cavity, wherein a wall of the smaller cavity is formed by a portion of the shell body and wherein said portion of the shell body includes a hole connecting the smaller cavity to the outside of the shell body, and further comprising an acoustical microphone mounted outside said driver cavity and in front of the driver, during use said microphone constructed and arranged to provide a feedback signal for an active noise reduction circuit.

23. The supra aural headphone of claim 22 wherein said microphone has a front side through which sound is received and it has a back side opposite said front side, said back side of the microphone including a pressure equalization hole formed therein, said headphone further comprising a conduit acoustically coupling said pressure equalization hole in the back side of the microphone to outside of said shell so as to prevent a direct acoustical coupling between the internal cavity and the hole in the back side of the microphone.

24. The supra aural headphone of claim 23 wherein the conduit passes into said driver cavity.

25. The supra aural headphone of claim 23 wherein the conduit passes through said shell body to the outside of said shell body.

26. A supra aural headphone including an earphone, said earphone comprising:

a shell body having an inside and an outside;

a cushion mounted on the shell, said cushion and the inside of said shell defining an internal cavity behind the cushion, said cushion having a passageway extending therethrough so as to acoustically connect said internal cavity with a user's ear cavity when the cushion is resting on the user's ear while being worn by the user, said internal cavity having a total volume that is a volume of at least about 40 cubic centimeters;

an acoustical driver constructed and arranged within said internal cavity to avoid obstructing the passageway which acoustically connects the internal cavity with the user's ear cavity, and wherein during use said driver reproduces sound for the user when driven by an audio electrical signal; and an acoustical microphone mounted adjacent to said acoustical driver outside said internal cavity, during use said microphone constructed and arranged to provide a feedback signal for an active noise reduction circuit.

27. The supra aural headphone of claim 26 wherein the total volume of the internal cavity is about 4 cc.

28. The supra aural headphone of claim 27 wherein the microphone is mounted in front of the driver and is offset from the center of the driver.

29. The supra aural headphone of claim 28 wherein the microphone lies in a first plane and the driver lies in a second plane and wherein the first plane is substantially perpendicular to the second plane.

30. The supra aural headphone of claim 29 wherein the cushion has a back side and a front side and wherein the passageway forms an opening in the back side and wherein the second plane is inclined with respect to the opening in the back side of the cushion.

31. The supra aural headphone of claim 30 wherein the second plane is inclined with respect to the opening in the back side of the cushion so that the microphone extends into the passageway.

* * * * *